United States Patent
Shimada et al.

(10) Patent No.: US 6,880,403 B1
(45) Date of Patent: Apr. 19, 2005

(54) STRUCTURE INSPECTION DEVICE

(75) Inventors: Takashi Shimada, Tokyo (JP); Kanji Matsuhashi, Hiroshima (JP)

(73) Assignees: Mitsubishi Denki Kabushiki Kaisha, Tokyo (JP); Matsuhashi Techno Research Co., Ltd., Hiroshima (JP)

( * ) Notice: Subject to any disclaimer, the term of this patent is extended or adjusted under 35 U.S.C. 154(b) by 54 days.

(21) Appl. No.: 10/070,379

(22) PCT Filed: Aug. 28, 2000

(86) PCT No.: PCT/JP00/05797

§ 371 (c)(1),
(2), (4) Date: Mar. 6, 2002

(87) PCT Pub. No.: WO02/18927

PCT Pub. Date: Mar. 7, 2002

(51) Int. Cl.⁷ .............................................. G01N 29/20
(52) U.S. Cl. .......................... 73/652; 73/600; 73/602; 73/643
(58) Field of Search ........................ 73/652, 658, 660, 73/665, 666, 668, 600, 644, 579, 602, 584, 73/598, 643, 578, 596, 627

(56) References Cited

U.S. PATENT DOCUMENTS

| | | | | |
|---|---|---|---|---|
| 3,580,056 A | * | 5/1971 | Warner | 73/579 |
| 3,859,847 A | * | 1/1975 | Ronemus | 73/660 |
| 3,867,836 A | * | 2/1975 | Sessler et al. | 73/629 |
| 4,163,393 A | * | 8/1979 | Gutierrez et al. | 73/584 |
| 4,185,180 A | * | 1/1980 | Anderson | 200/61.45 R |
| 4,479,389 A | * | 10/1984 | Anderson et al. | 73/651 |
| 4,599,898 A | * | 7/1986 | Beer | 73/579 |
| 4,679,033 A | * | 7/1987 | Hwang | 340/566 |
| 4,699,006 A | * | 10/1987 | Boxenhorn | 73/514.15 |
| 5,054,606 A | * | 10/1991 | Musschoot | 195/751 |
| 5,152,401 A | * | 10/1992 | Affeldt et al. | 209/556 |
| 5,442,961 A | * | 8/1995 | Bozeman, Jr. | 73/660 |
| 5,503,010 A | * | 4/1996 | Yamanaka | 73/105 |
| 5,612,495 A | * | 3/1997 | Shimada et al. | 73/579 |
| 5,808,202 A | * | 9/1998 | Passarelli, Jr. | 73/643 |
| 5,880,351 A | * | 3/1999 | Orita et al. | 73/1.82 |
| 6,234,022 B1 | * | 5/2001 | Tadokoro | 73/593 |
| 6,298,729 B1 | * | 10/2001 | Locker et al. | 73/668 |
| 6,553,837 B1 | * | 4/2003 | Lysen | 73/579 |
| 6,591,681 B1 | * | 7/2003 | Shimada et al. | 73/600 |
| 6,629,448 B1 | * | 10/2003 | Cvancara | 73/1.38 |

* cited by examiner

Primary Examiner—Hezron Williams
Assistant Examiner—Jacques M. Saint-Surin
(74) Attorney, Agent, or Firm—Sughrue Mion, PLLC

(57) ABSTRACT

An internal condition of a concrete structure is objectively evaluated irrespective of surrounding noise or the shape of a hammer, by placing a vibration sensor in direct contact with a measuring surface so as to directly convert a vibration generated on the measuring surface into a corresponding voltage without the intervention of a medium such as air thereby to quantify the vibration generated on the measuring surface concerned. A structure diagnosis apparatus of the present invention includes a vibration unit for generating an elastic wave in a measuring object of a concrete structure, a vibration detector adapted to be placed in contact with a surface of the measuring object for detecting a component in a predetermined frequency range of an elastic vibration generated on the surface of the measuring object by the vibration unit; and a display device for displaying a maximum amplitude of an output signal of the vibration detector.

14 Claims, 15 Drawing Sheets

(a)

(b)

(a)

(b)

(a)

(b)

STRUCTURE INSPECTION DEVICE

TECHNICAL FIELD

The present invention relates to an apparatus for detecting abnormalities or defects in the interior of a concrete structure.

BACKGROUND ART

FIG. 17 illustrates a conventional apparatus, disclosed in Japanese Patent Application Laid-Open No. 7-20097 for instance, for detecting the sound pressure level of a hammering or striking sound by means of a sound pressure detector such as a microphone thereby to find an internal defect or flaw based on the sound pressure level thus detected. In FIG. 17, 2001 designates a concrete product, 2003 a hammer device having a hammer head 2002, and 2005 a fast Fourier transform machine connected with a sound level meter 2004 and a display device 2006.

Now, reference will be made to the operation of the above-mentioned prior art. Conventionally, in such a destructive inspection, an inspector hits or strikes a measuring surface lightly with an inspection hammer so as to detect a defect, which may exist in the interior of a concrete structure, by a difference in the tone of a hammering sound generated at that time. This method is an inspection according to human senses, and hence the criterion for determination is not constant, so that variations in the inspection results would be caused due to the inspector's experience, intuition and the level of his or her skill, thus making vague the records of the inspection results.

Moreover, attempts have been made to apply a destructive inspection using supersonic waves, but the frequency band efficiently output by known probes is several hundred kHz or more, so the supersonic waves are liable to be scattered by aggregates in the interior of the concrete structure because of their wave length, and the range capable of being inspected has been limited to a shallow area from the surface. In addition, upon inspection, it is necessary to grind the measuring surface and coat it with grease or the like so that matching of the acoustic impedances can be effected to permit acoustic waves to be transmitted to the measuring object. As a consequence, a certain period of time is required for preparation of the measurement, thus giving rise to a problem for practicable workability.

As a method of quantitatively evaluating such an inspection by a hammering sound, Japanese Patent Application Laid-Open No. 7-20097 for instance discloses a method of identifying an internal defect with the level of the sound pressure of a hammering sound detected by a sound level meter. In such a conventional inspection apparatus, the concrete product 2001 is hitted or struck lightly with a fixed impulsive force by using the hammer device 2003 equipped with the hammer head 2002. The hammering sound generated at that time is collected by the sound level meter 2004, and converted into an electric signal. The hammering sound thus converted into the electric signal is recorded by the fast Fourier transform machine 2005, and output to the display device 2006.

An impact generated in the concrete product 2001 by striking becomes a vibration on the surface, which vibrates the air at the boundary surface, thereby propagating as a sound. This sound is converted into an electric signal through a sound collecting device such as the sound level meter 2004. In cases where there exists an abnormality with decreased mechanical strength in the interior of the concrete product 2001, the magnitude and frequency of the vibration generated on the surface are different from those in the case of a sound one without any abnormality, and the magnitude and frequency of the sound generated also differ accordingly. As a result, the internal defect can be detected by comparing the vibration frequency and the sound pressure level of the impulsive sound converted into the electric signal.

With such a conventional method, however, a resonance sound determined by the material and the shape of the hammer is generated from the hammer itself by an external impact and mixed with the striking sound on the measuring surface, so that different striking sounds can be observed at the same location depending upon the kind of the hammer, thus resulting in a failure or error in the abnormality determination. In addition, there has been another problem that the striking sound could not be identified or discriminated correctly if surrounding noise exceeds the level of the striking sound to a remarkable extent, or if the reverberation of the striking is mixed with the striking sound.

Moreover, the vibration generated on the measuring surface can be changed by the striking angle and the shape of the striking surface, and hence the characteristic of the impulsive sound generated might also be changed, thus sometimes causing a wrong diagnosis.

Further, the level of the striking sound detected could be changed greatly depending upon the distance between the point of striking and the sound collecting device, the direction therebetween, etc., so it is necessary to correct the installation position and the direction of the sound collecting device, or alter the settings of the criterion each time there takes place a change in the distance between the sound collecting device and the striking point.

Accordingly, there arises a further problem that in order to quantify the striking sound under a certain fixed criterion or standard to detect an internal abnormality, it is necessary to select the shape of the hammer and make the measurement environment constant.

DISCLOSURE OF THE INVENTION

The present invention is intended to obviate the problems as referred to above, and has for its object to provide a structure diagnosis apparatus and a structure diagnosis method which are capable of objectively evaluate the internal condition of a concrete structure irrespective of surrounding noise or the shape of a hammer, by placing a vibration detecting sensor in direct contact with a measuring surface so as to directly convert a vibration generated on the measuring surface into a corresponding voltage without the intervention of a medium such as air thereby to quantify the vibration generated on the measuring surface concerned.

According to one aspect of the present invention, there is provided a structure inspection apparatus comprising: a vibration unit for generating an elastic wave in a measuring object of a concrete structure; a vibration detector adapted to be placed in contact with a surface of the measuring object for detecting a component in a predetermined frequency range of an elastic vibration generated on the surface of the measuring object by the vibration unit; and a display device for displaying a maximum amplitude of an output signal of the vibration detector.

Preferably, the vibration detector comprises: a weight; a spring having one end thereof connected with a contactor which is adapted to be in contact with the measuring object, and the other end thereof connected with the weight; and a vibration sensor connected with the weight for converting a vibration of the weight into a corresponding electric signal. A resonance frequency determined by a mass of the weight and a spring constant of the spring is set to be within the predetermined frequency range, so that a component in the predetermined frequency range of an elastic vibration generated on the surface of the measuring object is detected by the vibration sensor.

Preferably, the vibration detector comprises: a spring connected with a contactor which is adapted to be in contact with the measuring object, the spring being made of a metallic material of which permeability is varied according to a bending distortion thereof; a coil arranged around the spring which acts as a core member; and a weight connected with the spring. A bending distortion produced in the spring by an elastic vibration generated on the surface of the measuring object is detected by the coil.

Preferably, the vibration unit comprises: a striking section for vibrating the measuring object thereby to generate an elastic wave; a coil fixed to the striking section; a diode connected with the coil for permitting a current to flow through the coil only in one direction; and a magnet fixedly arranged near the coil in the surroundings of the striking section for generating a magnetic field in a direction in which the coil vibrates. Damping is caused only in one direction of the vibration of the striking section by mean of an electromagnetic interaction between the magnet and the coil.

Preferably, the vibration unit comprises: a striking section for generating an elastic wave on the measuring surface; a chamber in which the striking section is accommodated; and a striking section operating mechanism for injecting a pressure medium into the chamber thereby to project the striking section outward from the chamber. The striking section operating mechanism generates an elastic wave on the measuring surface by applying thereto a fixed vibration force by means of the striking section.

Preferably, the striking section operating mechanism comprises: an injector for injecting a pressure medium into the chamber; and a pressure medium feeding mechanism for supplying a pressure medium to the chamber when a distance between the chamber and the measuring surface becomes a predetermined value.

Preferably, the pressure medium feeding mechanism comprises: a gas cylinder for reserving the pressure medium; a pressure regulator for regulating the pressure of the pressure medium in the gas cylinder; a supply switch for supplying the pressure medium in the gas cylinder to the injector through the pressure regulator; and a trigger mechanism for triggering the supply switch when the distance between the chamber and the measuring surface becomes a predetermined value.

Preferably, the pressure medium feeding mechanism comprises: a compressor connected with the injector for supplying the pressure medium thereto; a supply switch for supplying the pressure medium in the compressor to the injector; and a trigger mechanism for triggering the supply switch when the distance between the chamber and the measuring surface becomes a predetermined value.

Preferably, the pressure medium feeding mechanism further comprises a spring having one end thereof connected with a housing of the vibration unit and the other end thereof connected with the trigger mechanism for urging the trigger mechanism in a direction away from the supply switch.

Preferably, the display device comprises: an amplifier having an input terminal connected with the vibration detector and an output terminal; a plurality of comparators each having a first input terminal connected with the output terminal of the amplifier, a second input terminal to which a reference voltage is imposed and an output terminal, the comparators being arranged in parallel with one another and each generating an output from its output terminal when an input voltage at its first input terminal exceeds the reference voltage at its second input terminal; and a plurality of display members connected with the output terminals of the comparators, respectively. The reference voltages imposed on the output terminals of the comparators, respectively, are set to different values.

Preferably, the predetermined frequency range of the elastic vibration is several kHz or less.

According to another aspect of the present invention, there is provided a structure diagnosis method for detecting an internal defect in a concrete structure, the method comprising: a first step of generating an elastic wave on a measuring surface of a measuring object by applying a fixed force thereto; a second step of converting a vibration generated on the measuring surface in the first step into a corresponding electric signal thereby to calculate a maximum amplitude of a component in a predetermined frequency range of the electric signal; and a third step of comparing the maximum value of the electric signal with a preset threshold thereby to detect the existence or absence of an internal defect in the structure.

Preferably, the predetermined frequency range of the electric signal is several kHz or less.

Incidentally, note that the term "internal defect" as used in the present invention represents a part having a crack, a surface peel-off, a so-called honeycomb or the like, generated in the interior of a concrete structure, in which cement is non-uniform with the mixing ratio being lower than a predetermined range to increase the proportion of aggregate and hence decrease the mechanical strength to a value not greater than a predetermined range.

There is a relation between the vibration amplitude level of a part having an internal defect and that of a sound or normal part, as shown in FIG. 12, so that these parts can be discriminated from each other by the use of their vibration amplitude levels. In addition, for a defect such as a peel-off on a surface, a crack or the like generated in the interior of a concrete structure, the distance (depth) from the surface to a defective portion can be estimated from the relation illustrated in FIG. 13.

BEST MODE FOR CARRYING OUT THE INVENTION

Hereinafter, preferred embodiments of the present invention will be described while referring to the accompanying drawings.

Embodiment 1.

Figure 1:
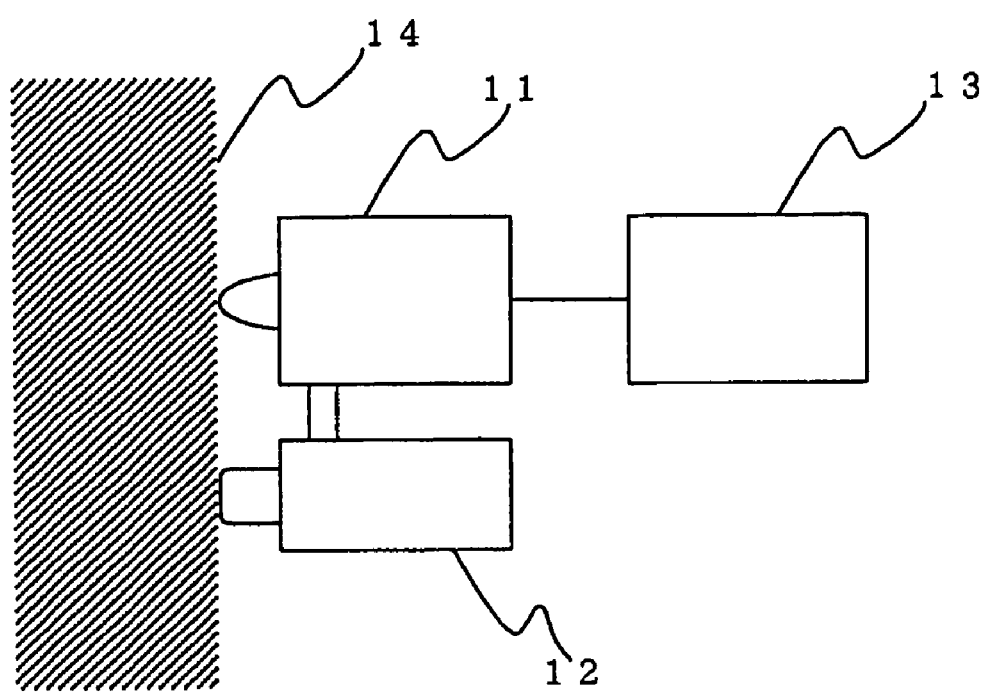
FIG. 1 is a block diagram illustrating the construction of a structure diagnosis apparatus according to a first embodiment of the present invention.

FIG. 1 is a block diagram illustrating the schematic construction of a structure diagnosis apparatus according to a first embodiment of the present invention. As shown in FIG. 1, the structure diagnosis apparatus according to the first embodiment includes a vibration detector 11 for detecting the vibration of a concrete structure 14, a vibration unit 12 by which vibration is applied to the concrete structure 14, and a display device 13 for displaying the vibration detected by the vibration detector 11.

Figure 2:
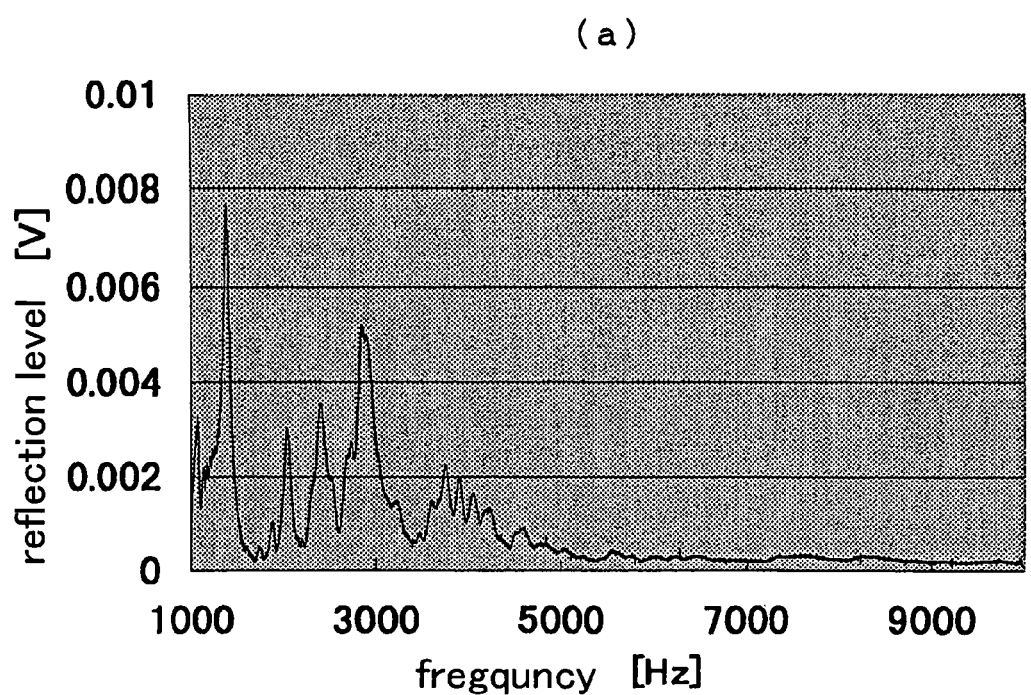
FIG. 2 is a waveform diagram illustrating a frequency response waveform upon striking of a concrete structure.
Figure 2:
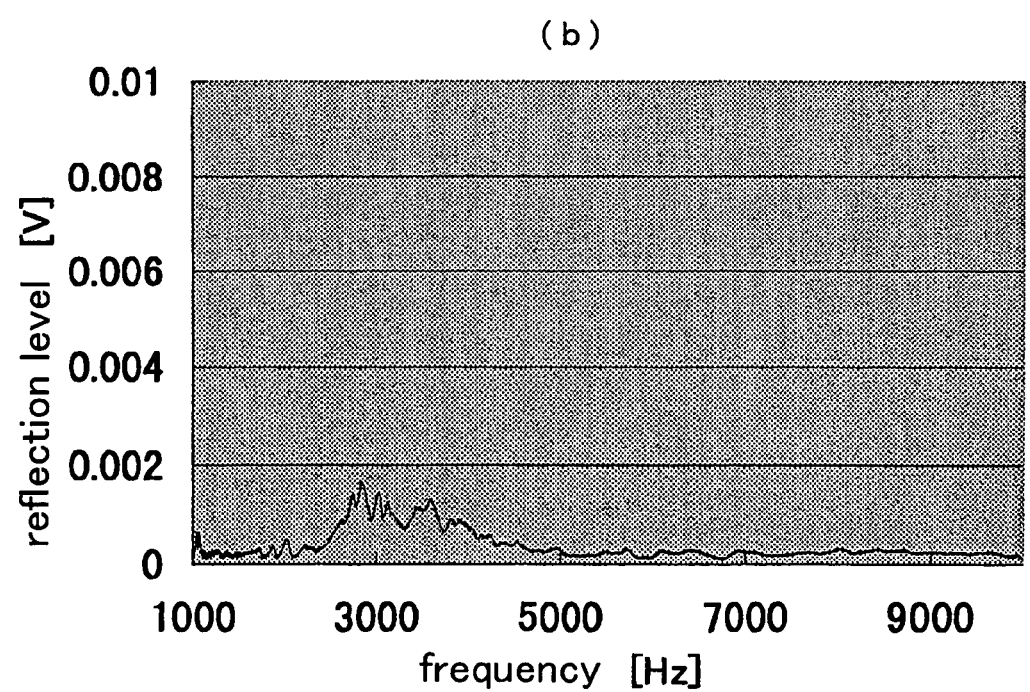
Figure 3:
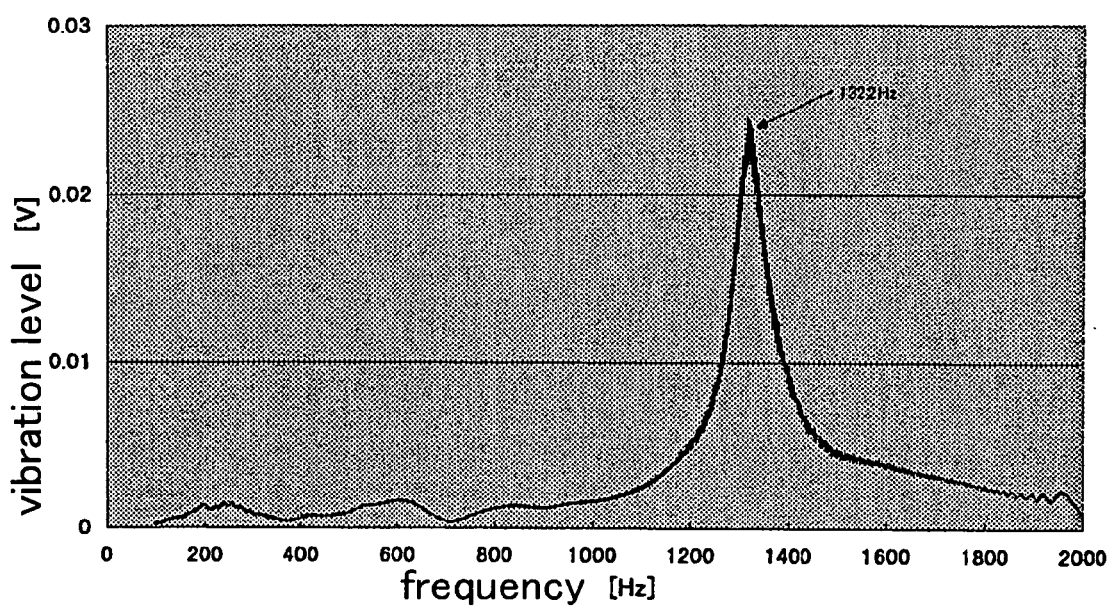
FIG. 3 is a waveform diagram illustrating the vibration characteristic of a vibration detector according to the present invention.

FIGS. 2(a) and 2(b) illustrate the vibration response conditions of the concrete structure 14 displayed by the display device 13, wherein FIG. 2(a) represents the vibration characteristic of a part having an internal defect, and FIG. 2(b) represents the vibration characteristic of a sound or normal part having no internal defect. FIG. 3 illustrates the vibration characteristic of the vibration detector 11.

Figure 4:
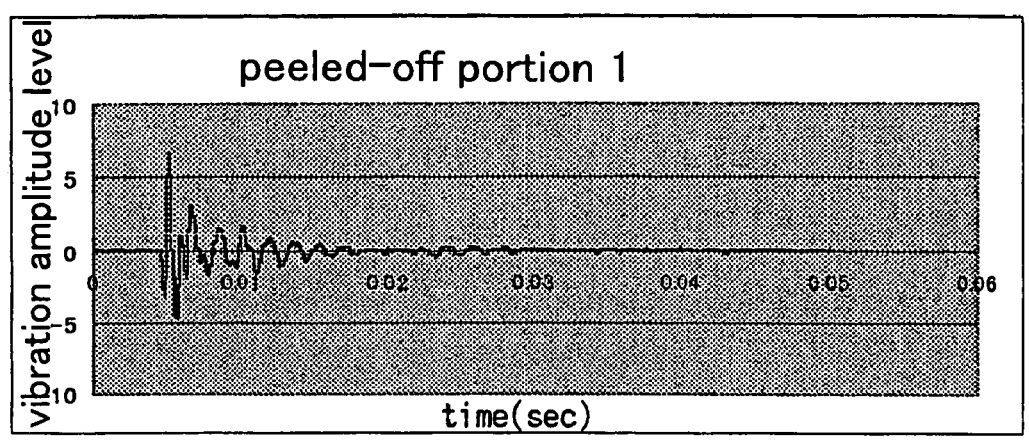
FIG. 4 is a waveform diagram illustrating a response waveform upon striking in cases where there is no internal defect in a concrete structure, according to the present invention.
Figure 4:
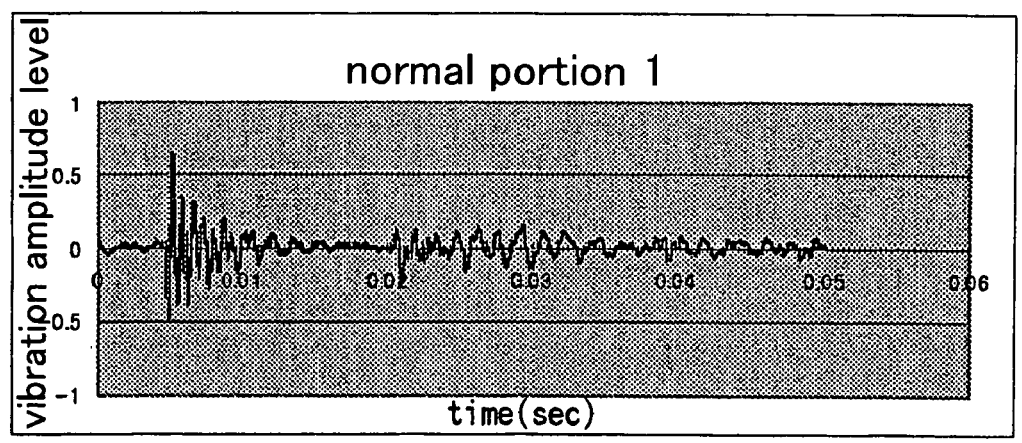
Figure 5:
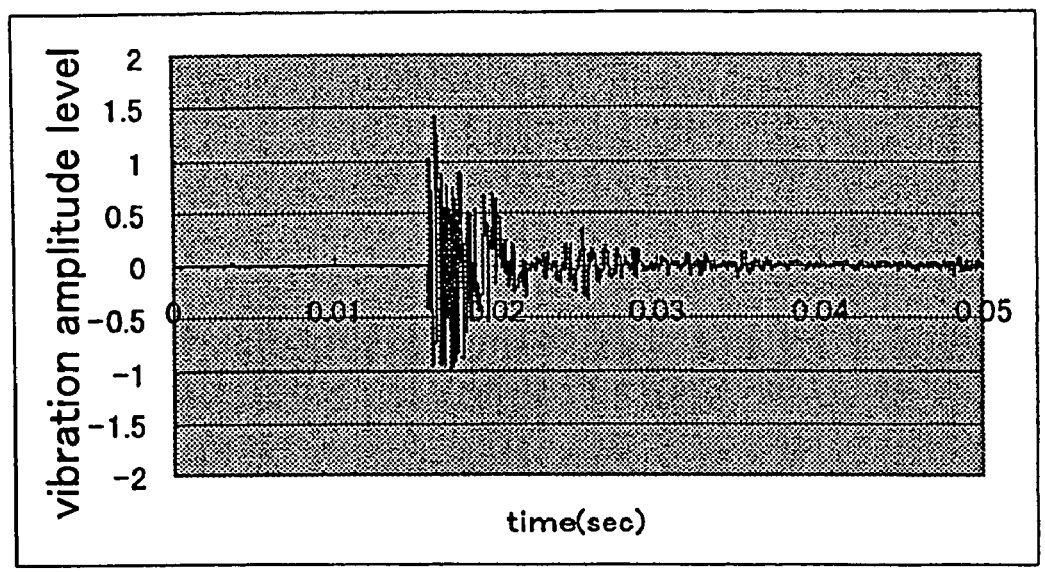
FIG. 5 is a waveform diagram illustrating a response waveform upon striking in cases where there is an internal defect in a concrete structure, according to the present invention.
Figure 5:
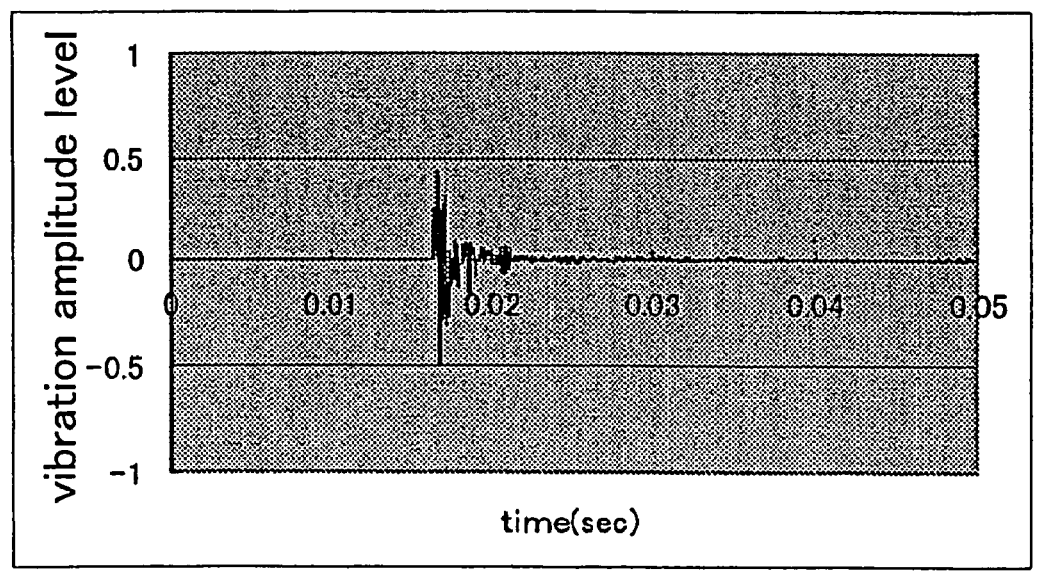

FIG. 4(a), FIG. 4(b), FIG. 5(a) and FIG. 5(b) are views illustrating, on a time base, waveforms which are detected by the vibration detector 11 as impulse responses of the concrete structure 14 when an iron ball of a fixed mass is dropped from a fixed height. FIG. 4(a) shows the vibration waveform of a part where an internal abnormality exists, and FIG. 4(b) shows the vibration waveform of a sound or normal part. On the other hand, FIG. 5(a) and FIG. 5(b) show the waveforms of the impulsive sounds which are generated at that time and detected by a microphone while respectively passing through band-pass filters with the same pass band. FIG. 5(a) represents a response observed in the part having the internal defect, and FIG. 5(a) represents a response observed in the sound part having no internal defect.

Figure 6:
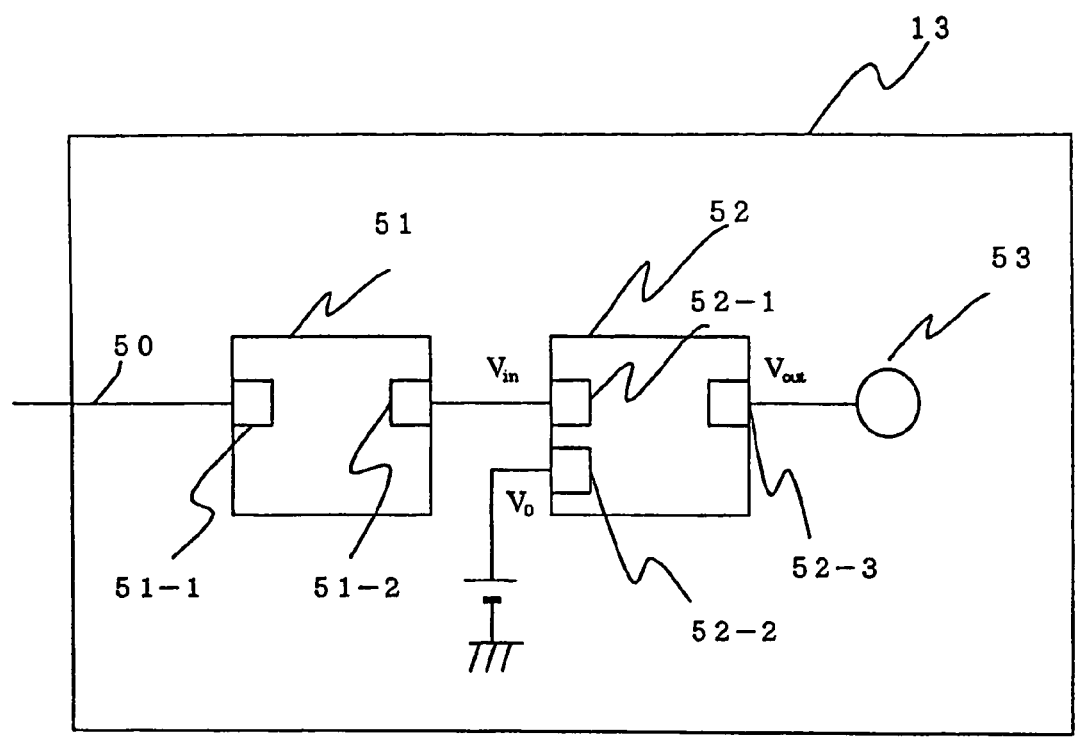
FIG. 6 is a block diagram illustrating one example of the construction of a display device according to the first embodiment of the present invention.

FIG. 6 is a block diagram illustrating one example of the construction of the display device 13. As shown in FIG. 6, the display 13 includes an amplifier 51 having an input terminal 51-1 connected with an input signal line 50, a comparator 52 having a signal input terminal 52-1 connected with an output terminal 51-2 of the amplifier 51 and a reference input terminal 52-2 connected with a reference power supply, and an LED 53 connected with an output terminal 52-3 of the comparator 52.

Figure 7:
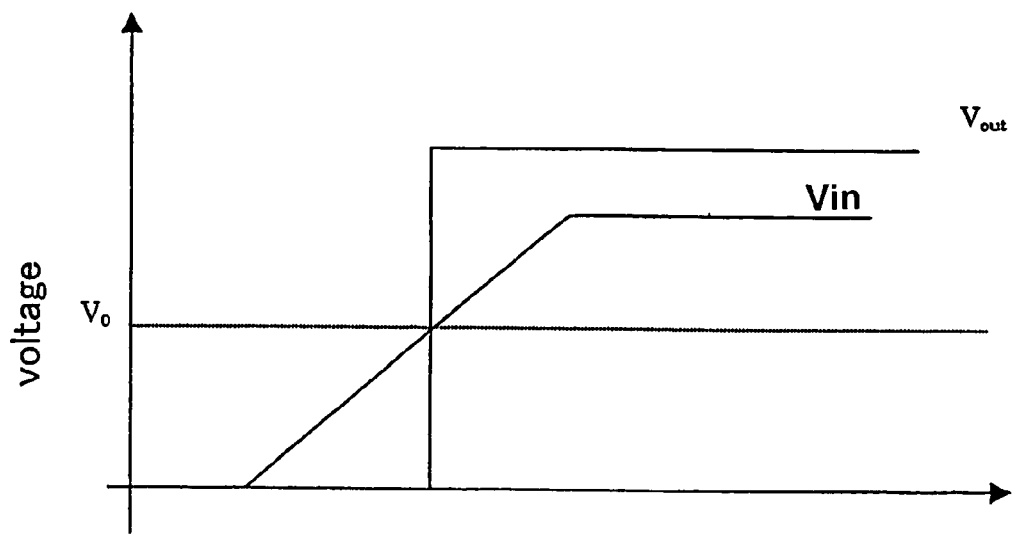
FIG. 7 is a graph illustrating the operation of the display device.

FIG. 7 illustrates a time base waveform showing the operation of the comparator 52, in which Vin represents an input voltage at the comparison signal input terminal 52-1 of the comparator 52; Vo represents a reference input voltage at the reference input terminal 52-2 of the comparator 52; and Vout represents a voltage at the output terminal 52-3 of the comparator 52, respectively.

Figure 8:
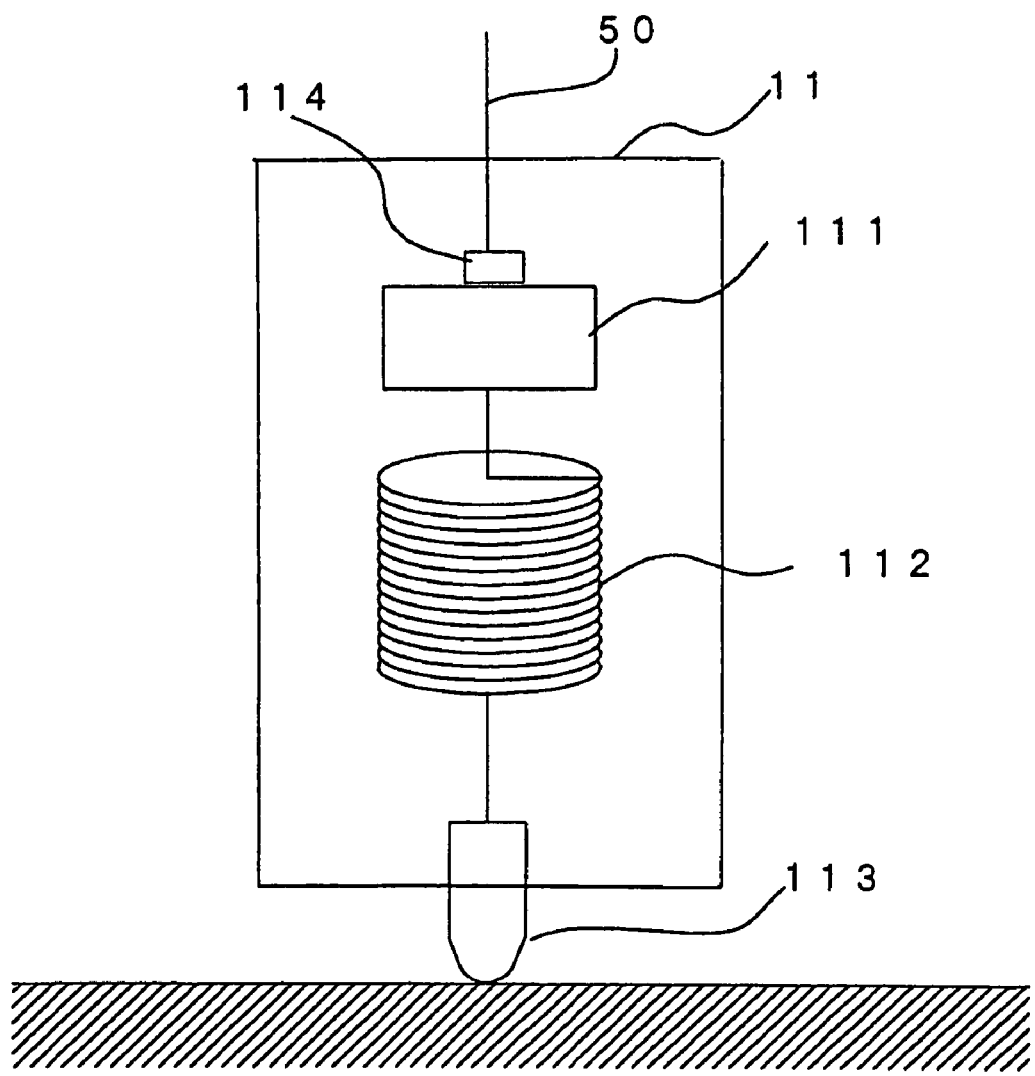
FIG. 8 is a view illustrating the schematic construction of a vibration detector according to the first embodiment of the present invention.

FIG. 8 is a view illustrating the construction of the vibration detector 11. The vibration detector 11 is constructed by connecting a contactor 113 with a weight 111 through a spring 112. The weight 111 is connected with the spring 112 and is placed in contact with a measuring surface through the contactor 113. A vibration/voltage transducer 114 is to convert a vibration into a corresponding voltage, and it is connected with the weight 111 for instance, so that a vibration arriving at the contactor 113 is transmitted therefrom to the vibration/voltage transducer 114 through the spring 112 and the weight 111. The vibration thus transmitted to the vibration/voltage transducer 114 is converted into a corresponding electric signal and then output from the vibration detector 11. The vibration/voltage transducer 114 is connected with the input signal line 50 of the display device 13, so that an output signal of the vibration/voltage transducer 114 is supplied to the display device 13 through the input signal line 50, whereby the result of the measurement is displayed by the display device 13.

In this case, assuming that the mass of the weight 111 is M and the spring constant of the spring 112 is k, this vibration system has a resonance frequency fo as represented by the following formula (1).

$$fo = (1/2\ \pi)(k/M)^{1/2} \tag{1}$$

When external vibrations are given to this system, the weight 111 produces a resonance phenomenon at the resonance frequency fo. That is, among the externally input vibrations, a component consistent to the resonance frequency fo is selectively emphasized. Thus, when the vibration/voltage transducer 114 such as an acceleration sensor is fixedly attached to the weight 111, a component of vibrations input from the contactor 113, which is consistent to the resonance frequency fo, is emphasized and output from the vibration detector 11.

Thus, by properly selecting the mass M of the weight 111 and the spring constant k of the spring 112 so as to adjust the resonance frequency fo to an optimal frequency of several kHz or less, it is possible to obtain the vibration detector 11 which can selectively detect a vibration component around that frequency and convert it into a corresponding electric signal.

Therefore, the filtering function for detecting the signal of a proper band becomes unnecessary, thus making it possible to use the display device 13 of a simpler circuit structure.

Moreover, a mechanical resonance system has a frequency response with a high Q value as compared with an electric potential resonance system, and hence it is possible to achieve a filtering effect of a narrow band. As a result, it is possible to realize a structure inspection apparatus which has excellent signal selectivity and is less subjected to the influence of external noise.

Figure 9:
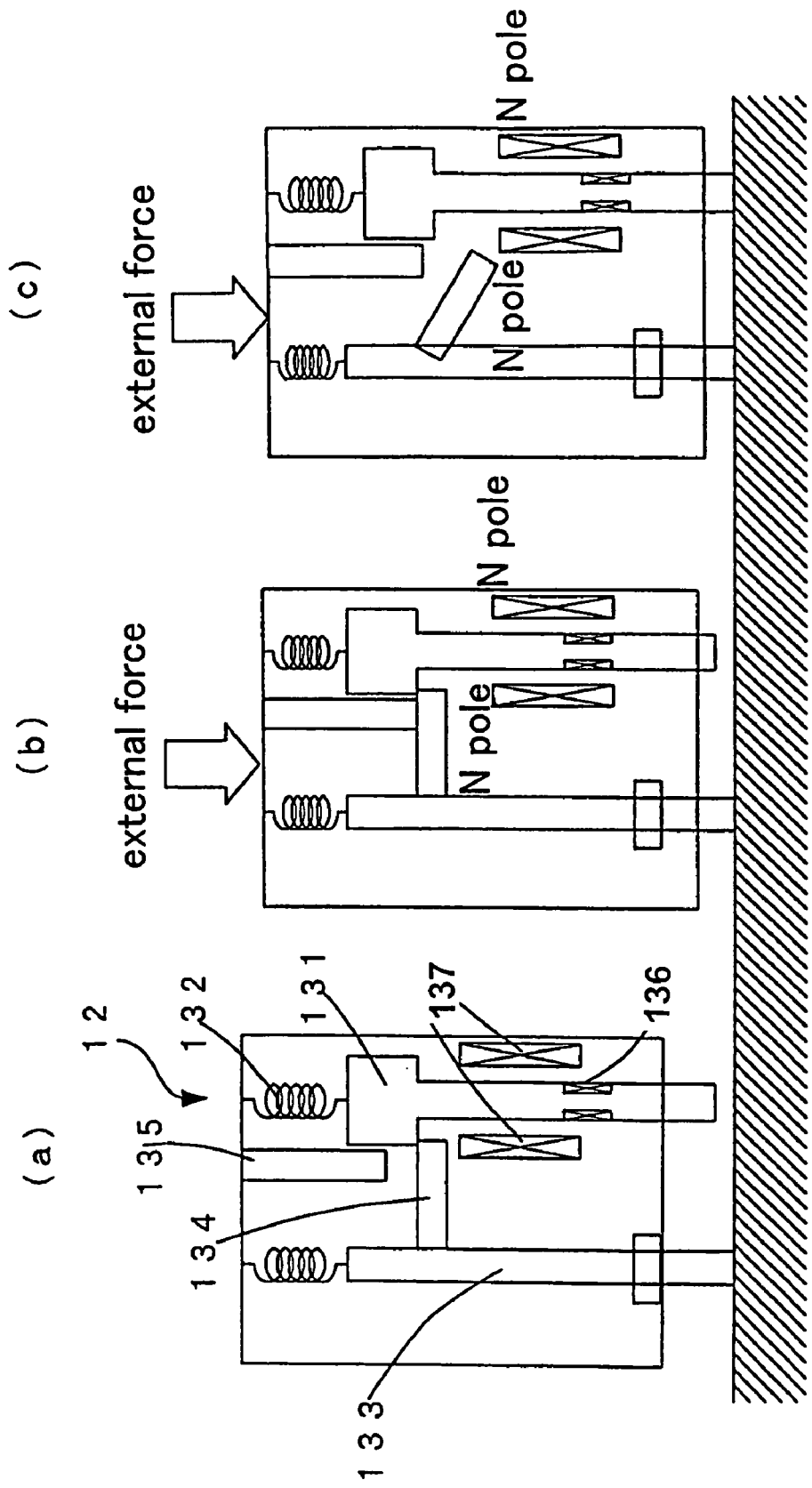
FIG. 9 illustrates the construction of a vibration unit according to the first embodiment of the present invention, in which (a), (b) and (c) represent different operating states thereof, respectively.

FIGS. 9(a)–9(c) illustrate one example of the vibration unit 12. In these figures, the vibration unit 12 includes a rod-shaped striking section 131, a spring 132 such as a coil spring connected with the striking section 131, a striking section latching mechanism 133 for latching the striking section 131, a release mechanism 134 rotatably mounted on the striking section latching mechanism 133 and urged by an unillustrated spring or the like to a latch position (FIG. 9(a)) in which it is placed into engagement with the striking section, a release trigger 135 mounted on the housing of the vibration unit 12 and arranged in opposition to the release mechanism 134, a permanent magnet 136 embedded in the outer peripheral portion of the striking section 131, and a coil 137 mounted on the housing of the vibration unit 12 and arranged adjacent the permanent magnet 136 so as to surround the striking section 131.

The striking section 131 is attached to the housing of the vibration unit 12 through the spring 132, and the spring 132 with no external force applied thereto has a nature length Lo.

When an external force is applied to the vibration unit 12, the striking section 131 latched by the striking section latching mechanism 133 begins to be moved in a direction to contract the spring 132 (FIG. 9(a)). With the external force being continuously kept applied, the striking section 131 and the striking section latching mechanism 133 continue to be moved in the contracting direction of the spring 132, so that the release mechanism 134 mounted on the striking section latching mechanism 133 will come into contact with the release trigger 135 attached to the housing of the vibration unit 12 (FIG. 9(b)). When the external force is further applied continuously, the release trigger 135 liberates or disengages the release mechanism 134 from the striking section 131, whereupon the striking section 131 is pushed out of the vibration unit 12 to strike the measuring surface under the action of the contraction energy of the spring 132 (FIG. 9(c)).

In this manner, by releasing the striking section 131 with the length of contraction of the spring 132 being fixed to a given length, the striking angle and the striking speed against the measuring surface can be made constant, thus making it possible to carry out a stable determination without personal dependency or variations.

In addition, the permanent magnet 136 fixedly secured to the housing of the vibration unit 12 generates a magnetic field in the contracting direction of the spring 132, so that a magnetic force acts on the coil 137, which is arranged in the surroundings of the striking section 131 in a direction to intersect the magnetic field generated by the permanent magnet 136, thereby causing the coil 137 and the striking section 131 released from the release mechanism 134 to vibrate together. As a result, there is developed an induced electromotive force in the coil 137, whereby a current corresponding to the vibration speed is caused to flow through the coil, generating a magnetic flux. Accordingly, there is always generated a magnetic force acting in a direction opposite the direction of vibration, thereby braking the vibration.

Figure 10:
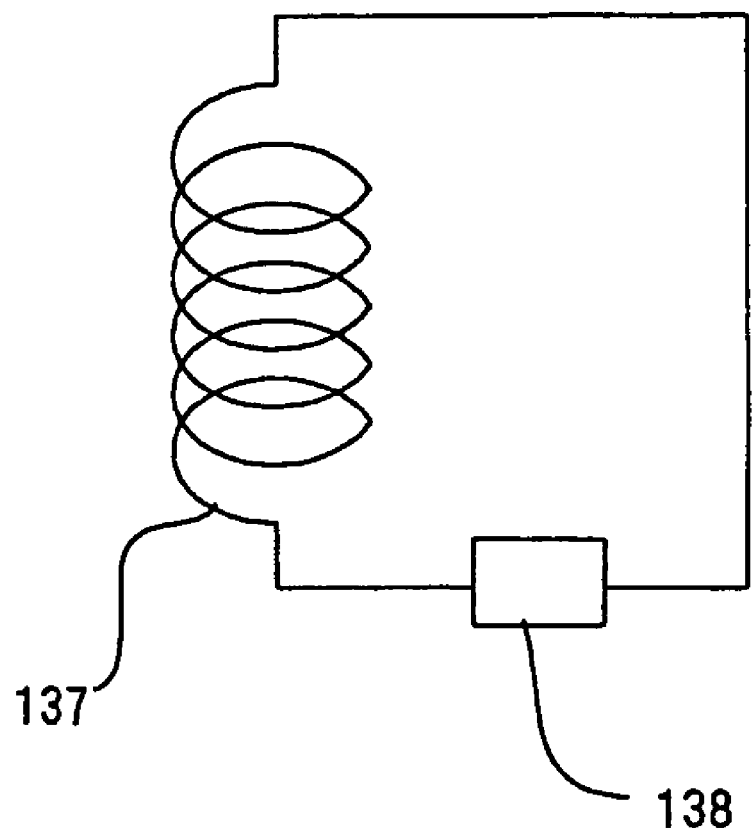
FIG. 10 is a partially enlarged view of the vibration unit.

Thus, a diode 138 is connected with the coil 137 in such a manner that a current is permitted to flow through the coil 137 when the spring 132 is contracted, but prevented from flowing when the spring 132 is pushed out to expand, as shown in FIG. 10. As a result, when the release mechanism 134 is liberated to permit the striking section 131 to be pushed out of the vibration unit 12, the striking section 131 is not braked by the coil 137, but can be braked when the striking section 131 starts to move in the contracting direction of the spring after striking.

As described above, by adjusting the speed upon striking, the expansion length, the spring constant or the like of the spring 132 upon striking, it is possible to prevent the measuring surface from being struck twice without loss of the striking energy, thus making it possible to repeat a constant impact continuously at the shortest time intervals.

In addition, if another coil is provided separately in the surroundings of the striking section 131, the speed of the striking section 131 can be detected by measuring a current, etc., generated in the coil when the striking section 131 is moving. Accordingly, by detecting the timing at which the striking section 131 (hammer) is released and by sampling the output of the vibration detector 11 in synchronization therewith, it is also possible to selectively obtain a signal corresponding to each striking with a reduced influence of external disturbances.

Next, reference will be made to the operation of the first embodiment. In order to perform measurements, the vibration detector 11 is brought into contact with an arbitrary point on a surface of the concrete structure 14 which is a measuring object. At this time, when an impact is applied to the surface of the concrete structure 14 (hereinafter referred to as a measuring surface) by means of the vibration unit 12, an elastic vibration is generated on the measuring surface. The vibration detector 11 detects the generated vibration and converts it into a corresponding electric signal. The vibration detector 11 has a function of outputting the electric signal according to the magnitude of vibration, and here it is shown that the greater the amplitude of the electric signal thus converted, the greater is the vibration generated. The electric signal converted by the vibration detector 11 is input to the display device 13. The display device 13 is constructed such that it detects the amplitude of the input electric signal and displays the magnitude or dimensions thereof.

If a defect such as a crack, a honeycomb, etc., which is deteriorated in the mechanical strength, exists in the interior of the concrete structure 14, vibration can be generated easily on a surface of the concrete structure by an external impact. At this time, when impulsive or striking energy is applied to the concrete structure from the exterior, there is generated a vibration whose amplitude varies according to the level of deterioration in the mechanical strength.

In fact, the vibration generated on a surface to which a vibration force of a given magnitude is applied was measured so that a comparison was made between the response of a part in which there occurred an internal crack and the response of a part in which no internal abnormality (defect) was identified. FIG. 2(a) represents the vibration characteristic of the part having an internal defect, and FIG. 2(b) represents the vibration characteristic of the part having no internal defect. In these figures, there are shown waveforms after the detected vibration is converted into an electric signal which is in turn subjected to frequency conversion, wherein the greater the amplitude level of each waveform, the greater is the amplitude of the vibration, too. From this, it is evident that a vibration component of a low frequency of several kHz or less becomes remarkable in the abnormal part in which there exists an internal defect. In comparison with the response of the sound or normal part at the same band, the magnitude of the response of the abnormal part reaches ten or more times that of the normal part, so it is understood that the levels of vibration in both parts are remarkably different from each other.

For instance, a high sensitivity characteristic having a center frequency at 1 kHz was given to the vibration detector 11, as shown in FIG. 3, and an iron ball of a fixed mass was dropped from a fixed height, thereby applying a fixed impulsive force to a measuring surface. When a vibration generated in the measuring surface at this time was detected by the vibration detector 11, it was observed that, as shown in FIG. 4(a), the part in which there exists an internal defect had a large vibration of an amplitude ten or more times greater than that of the part in which there exists no internal defect (FIG. 4(b)).

On the other hand, an external impact was similarly given to the same location, and an impulsive sound generated at that time was detected by a microphone so as to determine its response waveform. The response of the part where there exists an internal defect is illustrated in FIG. 5(a), and the response of the sound or normal part is illustrated in FIG. 5(b), respectively. In this case, a great difference in the amplitude between these parts as shown in FIGS. 4(a) and 4(b) was not seen. In addition, by changing the point of striking, the distance and direction of the microphone, some cases were seen in which the part having an internal defect exhibits a response waveform substantially the same as the level of the sound or normal part, and the opposite cases were also seen. Therefore, it is found that in order to distinguish these parts from each other according to the amplitude level of the sound observed, it is necessary to adjust the magnitude of striking, the position of detection, the directivity of the microphone, etc., in a detailed manner.

Thus, if the measuring surface is caused to vibrate by an external impact and the vibration generated on the measuring surface is measured directly without the intervention of air, neither external noise nor the resonance sound of the hammer will be transmitted to the measuring surface concerned, and hence these noise and sound do not become impediments to the measurements. Moreover, if the vibration of a frequency band specific to a defective portion is selectively detected and a determination is made according to the level of the vibration detected, even where the striking angle of the hammer or the shape of the striking surface changes so that there are generated vibration components hindering the evaluation outside the specific band concerned, such vibration components are attenuated, making it possible to perform a correct determination.

The display device 13 has a function of displaying an maximum amplitude of an electric signal input thereto, so that a part in which there exists an internal defect can be specified by comparison of the maximum amplitude displayed. FIG. 6 is a block diagram illustrating the construction of the display device 13, in which an electric signal converted by the vibration detector 11 is input to the input signal line 50. The input signal line 50 is connected with the input terminal 51-1 of the amplifier 51 so that the amplitude of the input signal is amplified by the amplifier 51 with a proper amplification factor, output from the output terminal 51-2, and supplied to the comparison signal input terminal 52-1 of the comparator 52. On the other hand, a reference voltage Vo is given to the reference input terminal 52-2 of the comparator 52. A display device such as, for instance, the LED 53 is connected with the output terminal 52-3 of the comparator 52.

As shown in FIG. 7, the reference voltage Vo of a constant value is always given to the reference input terminal 52-2, so that when the voltage Vin at the comparison signal input terminal 52-1 exceeds the reference voltage Vo, the output terminal 52-3 of the comparator 52 outputs a preset voltage Vout0. The output device such as, for instance, the LED 53 is connected with the output terminal 52-3 of the comparator 52, so that when the voltage at the output terminal 52-3 reaches Vout, a current flows to turn the LED 53 on.

It is considered that a hammer used by an inspector, a mechanical striking mechanism or the like is adopted as the vibration unit 12, but manual striking has a limitation on the stability of a vibration force generated, and if a mechanism for generating vibration with a constant force by means of a mechanical striking device is adopted, it will be possible to make an accurate determination with further reduced personal dependency or variations. In addition, by recording and preserving an output signal which is converted into an electric signal by the vibration detector 11, it becomes possible to quantitatively find a change over time of an internal abnormality (defect), which would be difficult to detect in conventional hammering tests using a hammer.

As described above, according to this first embodiment, since the vibration generated on the measuring surface can be directly observed, it is possble to obtain the result of inspection irrespective of inspector's skill or personal dependency or variations by quantifying hammering or striking tests without subject to the influence of diffusion or attenuation of sounds transmitting through a medium such as air, the interference of external noise, etc. In addition, since the vibration detector has a characteristic of selectively detecting a frequency component of several kHz or less, it is possible to effectively detect the vibration of a frequency of several kHz or less specifically generated in the part where there exists an internal defect likely to produce dull sounds. As a result, a structure diagnosis apparatus can be achieved which is capable of easily distinguish the part having an internal defect from the part where there exists no internal defect.

Embodiment 2.

Figure 11:
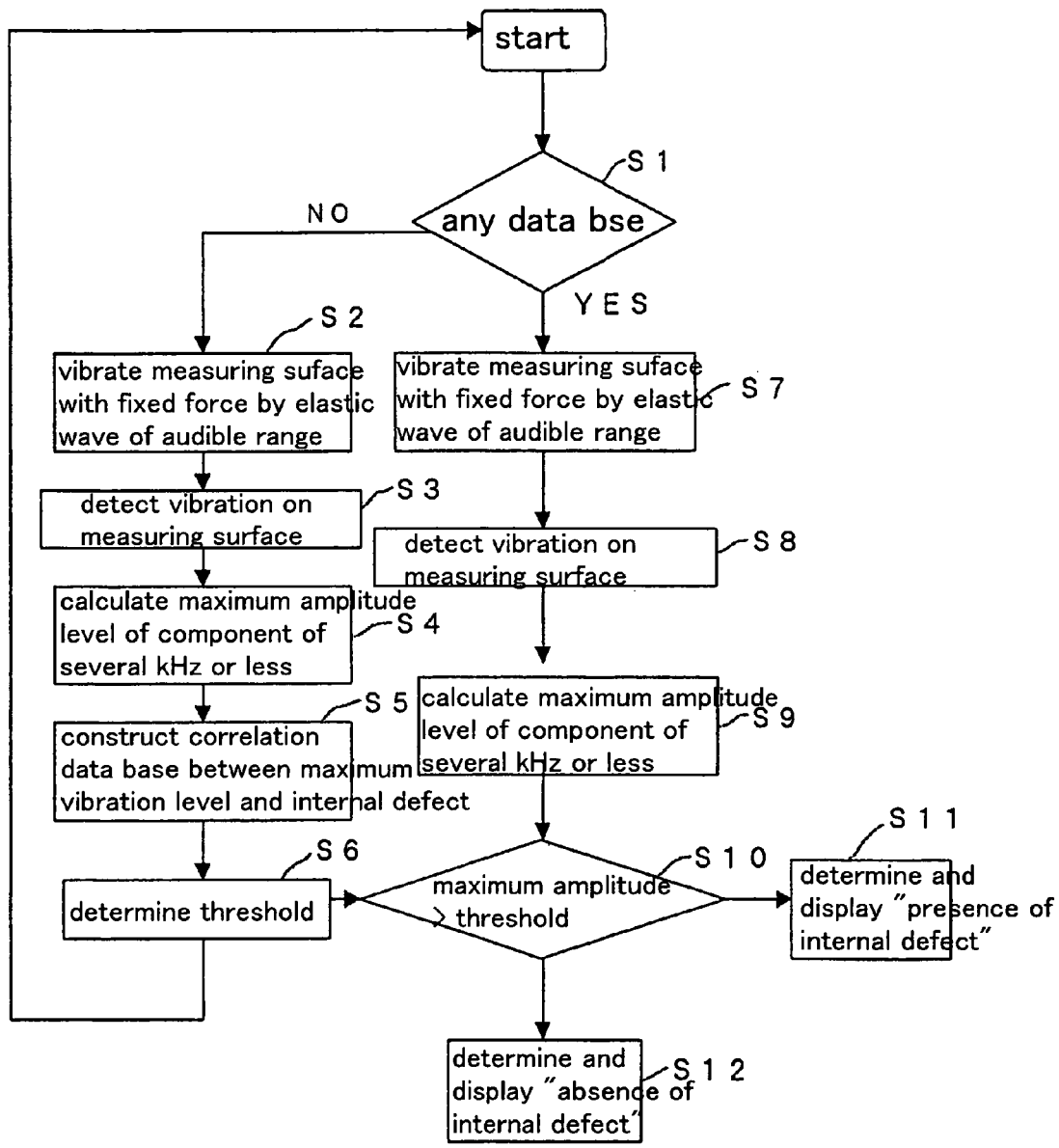
FIG. 11 is a flow chart illustrating a structure diagnosis method according to a second embodiment of the present invention.
Figure 12:
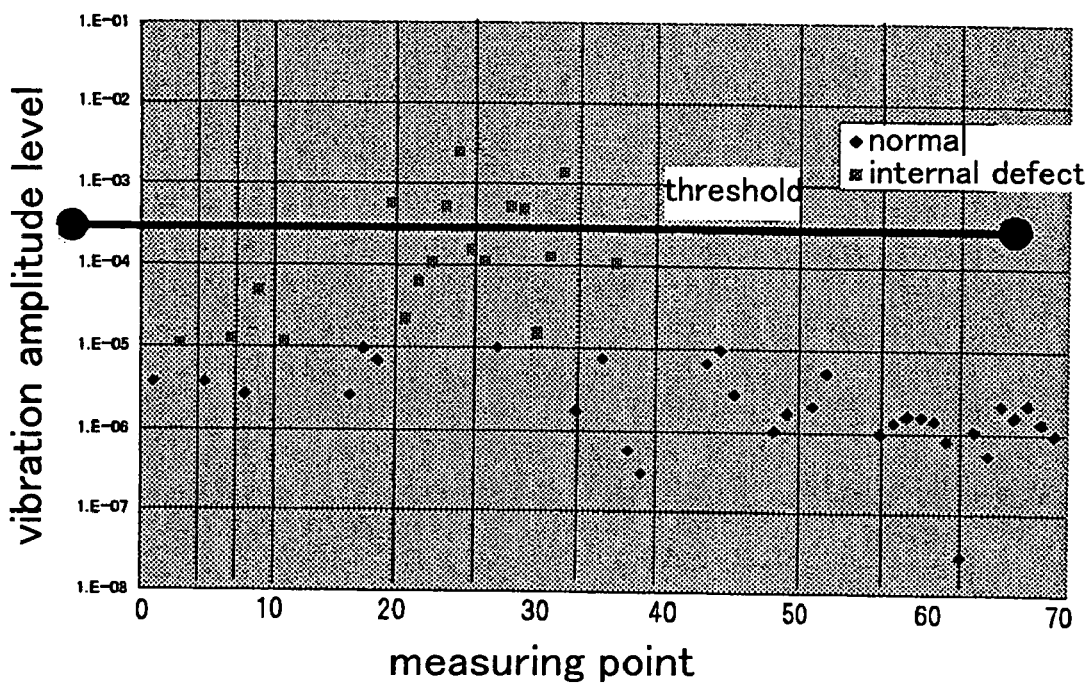
FIG. 12 is a view illustrating the relation between the vibration amplitude level of a concrete structure and an internal defect therein according to the present invention.
Figure 13:
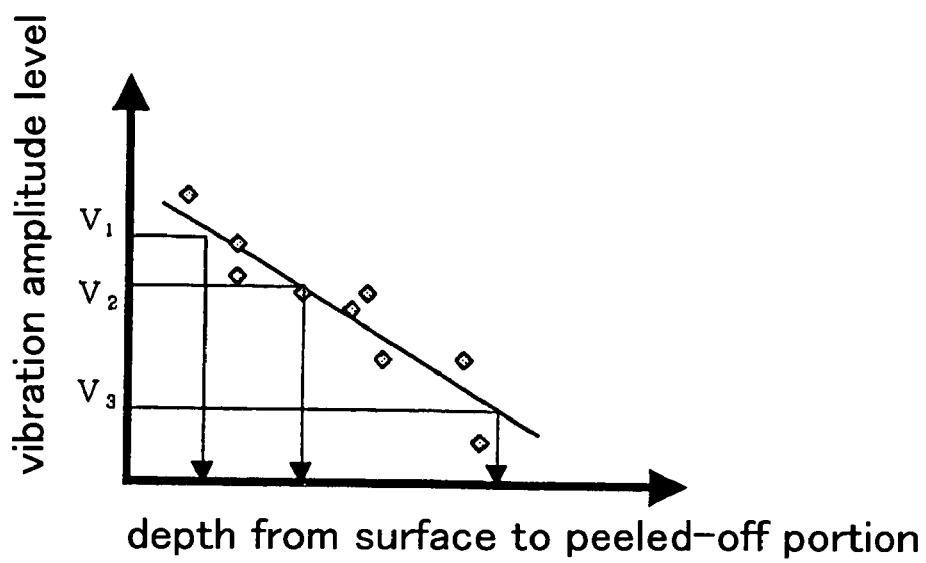
FIG. 13 is a view illustrating the relation between the vibration amplitude level of a concrete structure and the distance from a measuring surface to an internal defect according to the present invention.

Hereinafter, reference will be made to a structure diagnosis method according to a second embodiment of the present invention while referring to FIGS. 11 through 13. FIG. 11 is a flow chart illustrating a method of diagnosing an internal defect in a concrete structure according to the present invention. FIG. 12 is a graph illustrating the amplitude levels of vibrations produced by vibrating a part having an internal defect and a part having no internal defect with application of a fixed force. FIG. 13 is a graph illustrating the relation between the amplitude levels of vibrations and the distances (depth) from a measuring surface to internal defects measured in a part where there exist internal defects.

The diagnosis of an internal defect in a concrete structure is carried out by using the above-mentioned structure diagnosis apparatus according to a procedure as shown in the flow chart of FIG. 11. First of all, it is determined whether a data base concerning the vibration level of a normal part and an abnormal part exists (step S1). If such a data base does not exist, an impact is given to the abnormal part where there exists an internal defect and the normal part, respectively, by the vibration unit 12 which generates a constant vibration force (step S2), so that the levels of the vibrations generated in the respective parts are detected (step S3). A maximum amplitude level of a component in a predetermined frequency range (preferably, several kHz or less) is calculated (step S4) to construct a data base concerning the vibration levels of the normal part and the abnormal part (step S5). For instance, as illustrated in FIG. 12, the amplitudes of the vibrations measured on the surface of the structure are determined, and the internal state of the structure is checked by coring a measuring point concerned of the structure, so that the results of the measurements are ploted on a graph illustrating the relation therebetween (step S6).

Then, when the above-mentioned data base exists in step S1, an impact is given to a new inspection point or location by means of the vibration unit 12 with a vibration force equal to that in the above-mentioned inspection (step S7). The level of a vibration generated is measured (step S8), and the maximum amplitude level of a component in the above-mentioned predetermined frequency range is calculated (step S9), and compared with the threshold previously calculated (step S10). As a result, when the level of the measured vibration is greater than the threshold, it is determined that an abnormality exists in the interior of the structure (step S11). On the other hand, when the level of the measured vibration is smaller than the threshold, it is determined that the part inspected is normal (step S12). As seen from FIG. 12, a comparison between the levels of the vibrations generated in the normal part and in the abnormal part having an internal defect shows that they exist separately with a predetermined threshold being made as a boundary.

Thus, in FIG. 12, if the threshold for making a discrimination between the normal part and the abnormal part having an internal defect is set to Vo, thereafter, when the part having an internal defect is caused to vibrate by the same impulsive force as before, the level of a signal input to the display device 13 exceeds this threshold Vo, whereby LED 53 is turned on, making it possible to determine the existence of an internal defect in the interior of the structure.

Although the above-mentioned threshold is constructed so as to make discrimination between the normal part and the abnormal (defective) part, the response of the abnormal part varies in the level of vibration generated according to the materials, dimensions and depth of the abnormal part FIG. 13 illustrated the result of investigating a relation between the magnitude of vibration and the distance from a surface to a peeled off portion (part where aggregate, etc., is peeled off from the surrounding cement) as one example of an abnormal part, according to a similar procedure, wherein it is turned out that there is a strong correlation therebetween. Then, if the thresholds corresponding to the depths of peeled off portions are set to reference voltages $V_1$, $V_2$ and $V_3$ of comparators $52_1$, $52_2$ and $52_3$, respectively, of FIG. 16, it is possible to find the distances to the internal defects by the number of lit LEDs 53, that is, in four stages in this case.

If an event having a strong correlation to a detected vibration level is found among other events, a correlation formula representing a relation therebetween is determined experimentally or deductively according to a similar procedure, so that the event concerned is collated with a vibration level newly measured, thus making it possible to detect the internal state of the structure, which could not be evaluated in the past.

As described above, according to this second embodiment, since the vibration generated on the measuring surface can be directly observed with application of a fixed level of vibration force, it becomes possible to obtain information on the interior of a structure by comparing the level of the vibration thus measured with the data base measured in advance without subject to the influence of diffusion or attenuation of sounds transmitting through a medium such as air, the interference of external noise, etc.

Embodiment 3.

Figure 14:
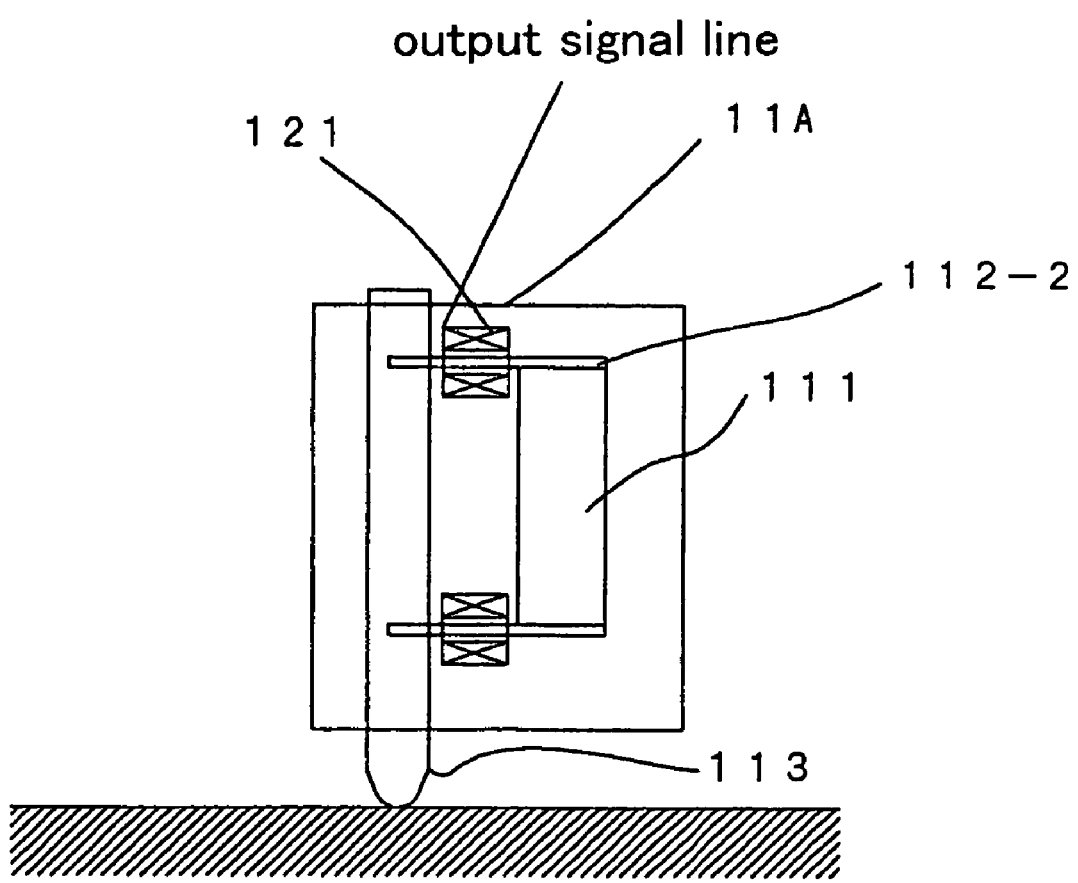
FIG. 14 is a view illustrating the construction of a vibration detector according to a third embodiment of the present invention.

Hereinafter, reference will be made to a structure diagnosis apparatus according to a third embodiment of the present invention while referring to FIG. 14. FIG. 14 illustrates an example in which a vibration detector 11A is comprised of a plate spring, with the remaining construction of this embodiment being similar to that of the aforementioned first embodiment. In FIG. 14, a weight 111 is connected with a contactor or probe 113 through plate springs 112-2, and a coil 121 is wound around each of the plate springs 112-2 for converting a change in magnetic permeability into a corresponding electric signal. A vibration arriving at the contactor 113 is transmitted to the weight 111 through the plate springs 112-2. At this time, as illustrated in the aforementioned third embodiment, a resonance frequency fo determined by the spring constant k of each plate spring 112-2 and the mass M of the weight 111 is calculated by the above-mentioned formula (1).

The plate springs 112-2 are made of a material such as a metallic magnetostrictive material, of which permeability changes according to an amount of distortion or strain given thereto. When a vibration given to the contactor 113 is transmitted to the weight 111, there is generated a bending distortion or strain in the plate springs 112-2, according to which the permeability of the magnetostrictive material changes. As the coils 121 are arranged in the surroundings of the plate springs 112-2, which are made as cores, respectively, an electromotive force is generated in each coil 121 according to a change in permeability of each core. The greater the bending distortion generated in the magnetostrictive material, the greater becomes the change in permeability. As a result, the voltage generated in each coil 121 also increases, so that a voltage or an electric signal can be obtained corresponding to the magnitude of the vibration transmitted to the weight 111.

As described above, according to this third embodiment, since the vibration transmitted to the weight 111 is directly detected by means of the plate springs 112-2 connected therewith, it is possible to obtain the vibration detector 11A which has a smaller vibration detection delay, as compared with the case where the vibration/voltage transducer 114 such as an acceleration sensor is fixedly attached to the weight 111 for generating an output. Moreover, it is unnecessary to fixedly attach the vibration/voltage transducer 114 such as an acceleration sensor to the weight 111, so it becomes possible to obtain the vibration detector 11A which is small in size, light in weight, low in cost, and high in sensitivity.

Embodiment 4.

Figure 15:
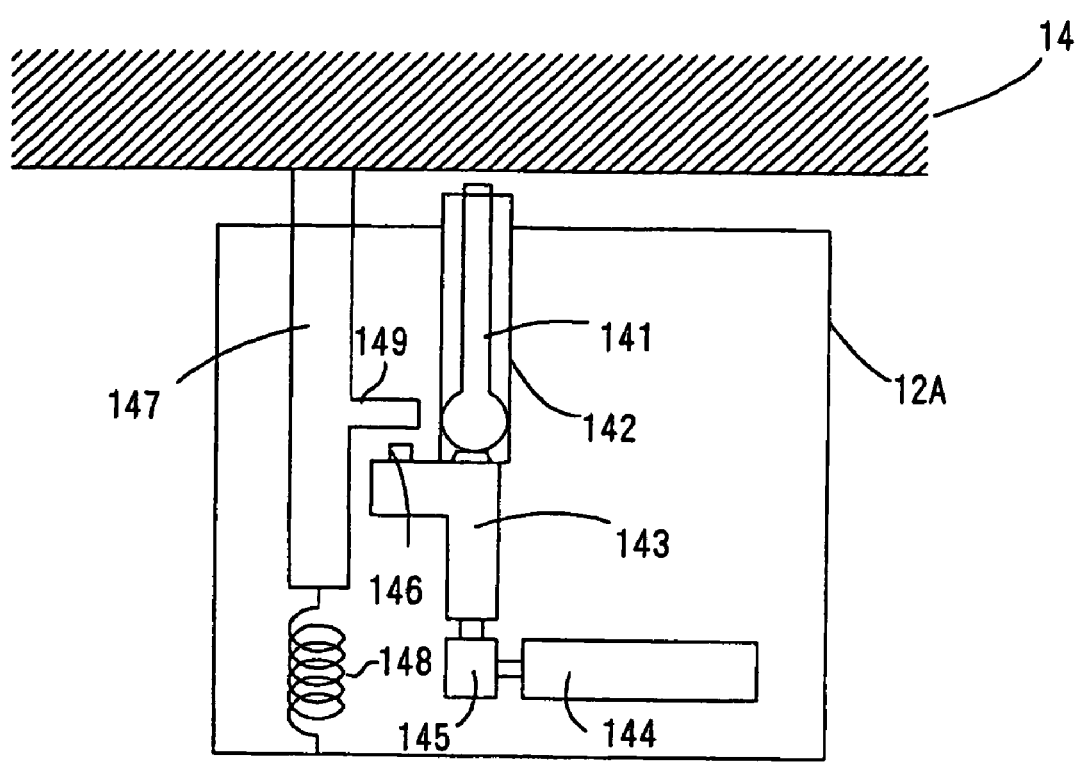
FIG. 15 is a view illustrating a vibration unit according to a fourth embodiment of the present invention.

Hereinafter, reference will be made to a structure diagnosis apparatus according to a fourth embodiment of the present invention while referring to FIG. 15. FIG. 15 illustrates another example of a vibration unit, with the remaining construction of this fourth embodiment being similar to that of the aforementioned first embodiment.

In FIG. 15, a vibration unit 12A includes a rod-shaped striking section 141 having one end thereof formed into a ball or spherical shape, a cylindrical chamber 142 having an open end opposed to a measuring surface of a concrete structure 14 and the other end closed, with the striking section 141 being accommodated therein, an air injector 143 arranged at the closed end of the chamber 142 for injecting compressed air into the chamber 142, a gas cylinder 144 connected with the air injector 143 through a pressure regulator 145, a compressed air supply switch 146 provided to the air injector 143, and a trigger mechanism 147 connected with the housing of the vibration unit 12A through the spring 148 and having a switch operation section 149 for operating or triggering the compressed air supply switch 146.

A clearance between the outer diameter of the striking section 141 and the inner diameter of the chamber 142 is narrow enough so that when compressed air is supplied from the air injector 143 to the chamber 142, the striking section 141 is pushed out by the pressure of the compressed air to project outward from the open end of the chamber 142.

The compressed air is reserved in the gas cylinder 144 and supplied to the air injector 143 with the pressure thereof being properly adjusted by the pressure regulator 145.

When the open end of the chamber 142 is caused to approach the measuring surface of the concrete structure 14, the trigger mechanism 147 is placed into abutting engagement with the measuring surface so that it is caused to move in a direction to enter the housing of the vibration unit 12A against the urging force of the spring 148. Together with this movement, the switch operation section 149 mounted on the trigger mechanism 147 is brought into abutment against the compressed air supply switch 146 to push it down, whereby the compressed air is supplied from the air injector 143 to the chamber 142, causing the tip end of the striking section 141 to project outward from the open end of the chamber to impinge against or strike the measuring surface of the concrete structure 14.

In this case, it may be constructed such that when the trigger mechanism 147 is moved relative to the housing of the vibration unit 12A to reach a point at which the distance between the chamber 142 and the measuring surface is a predetermined value, the compressed air supply switch 146 is pressed to supply the compressed air. With this construction, the striking section 141 is operated to strike the measuring surface at any time while holding the open end of the chamber 142 at the predetermined distance apart from the measuring surface, so it becomes possible to apply a fixed vibration force to the measuring surface concerned.

In addition, if it is constructed such that the trigger mechanism 147 is connected with the housing of the vibration unit 12A through the spring 148 for example, as shown in FIG. 15, the trigger mechanism 147 is permitted to return to the initial position by separating the vibration mechanism 12 from the measuring surface, so that compressed air can be repeatedly supplied by bringing the vibration unit 12A close to the measuring surface again. Similarly, a return mechanism such as a magnet, a spring or the like may be mounted on the striking section 141 for returning the striking section 141 to the initial position after striking, whereby it is possible to provide the vibration mechanism 12A capable of repeatedly performing striking. There are a variety of methods for triggering the compressed air supply switch 146 by means of the trigger mechanism 147, and hence the same function can be achieved by using a manual switch or an electromagnetic switch.

Moreover, there has been described the example of supplying compressed air by means of the gas cylinder 144 mounted on the vibration unit 12A, but if compressed air is separately supplied by a compressor instead of the gas cylinder 144, it becomes possible to repeat striking regardless of the capacity of the gas cylinder 144, or easily adjust the pressure of compressed air. Additionally, the vibration mechanism 12A can be easily reduced in size, thus further facilitating handling and manipulation thereof.

As described above, according to this fourth embodiment, it is possible to realize the vibration unit 12A which is convenient and small-sized, and provide a structure diagnosis apparatus which is capable of repeatedly striking a measuring surface with a constant vibration force. Further, it is also possible to easily control the vibration force by adjusting the pressure of compressed air.

Embodiment 5.

Figure 16:
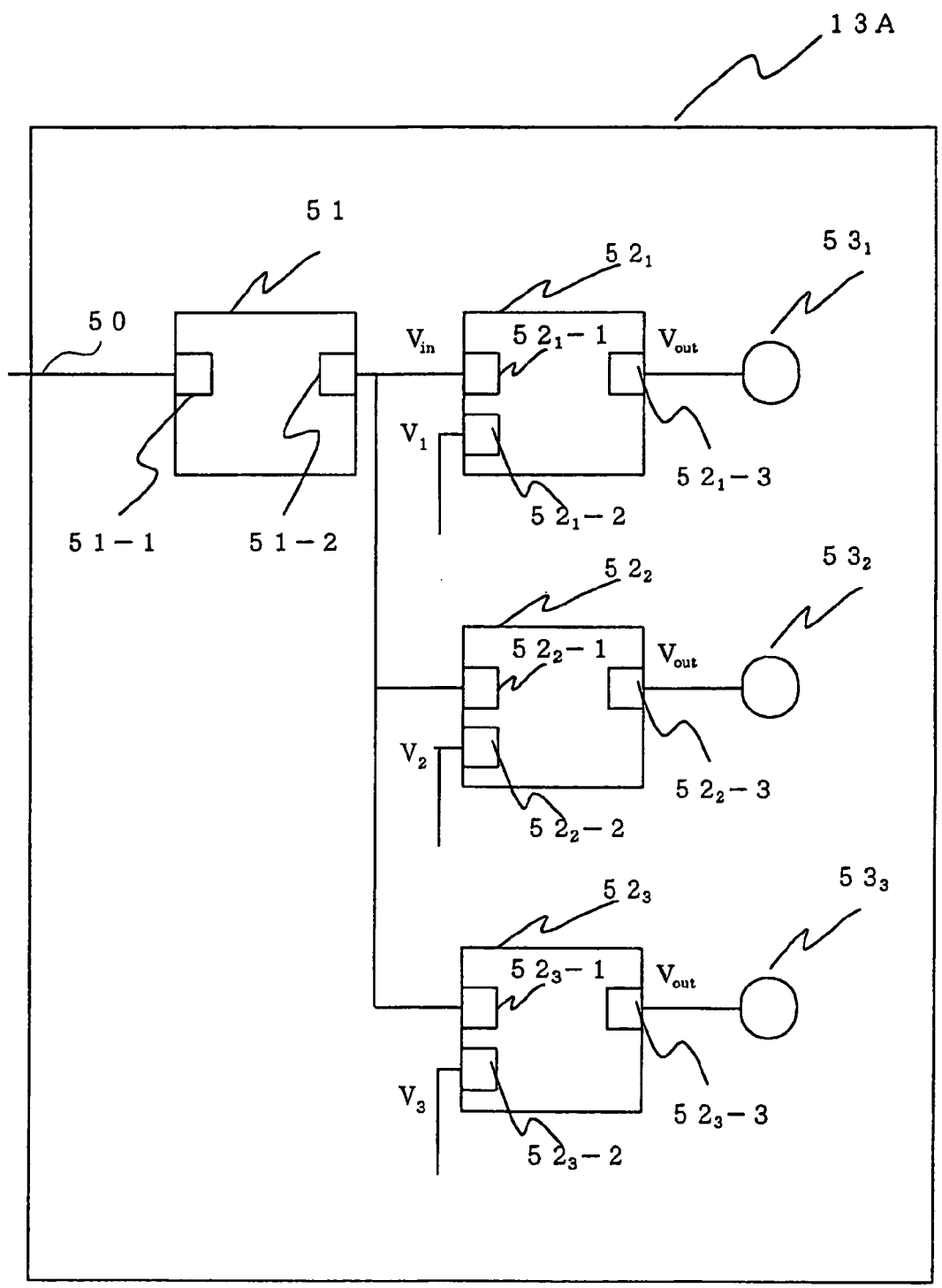
FIG. 16 is a block diagram illustrating another example of the construction of a display device according to a fifth embodiment of the present invention.
Figure 17:
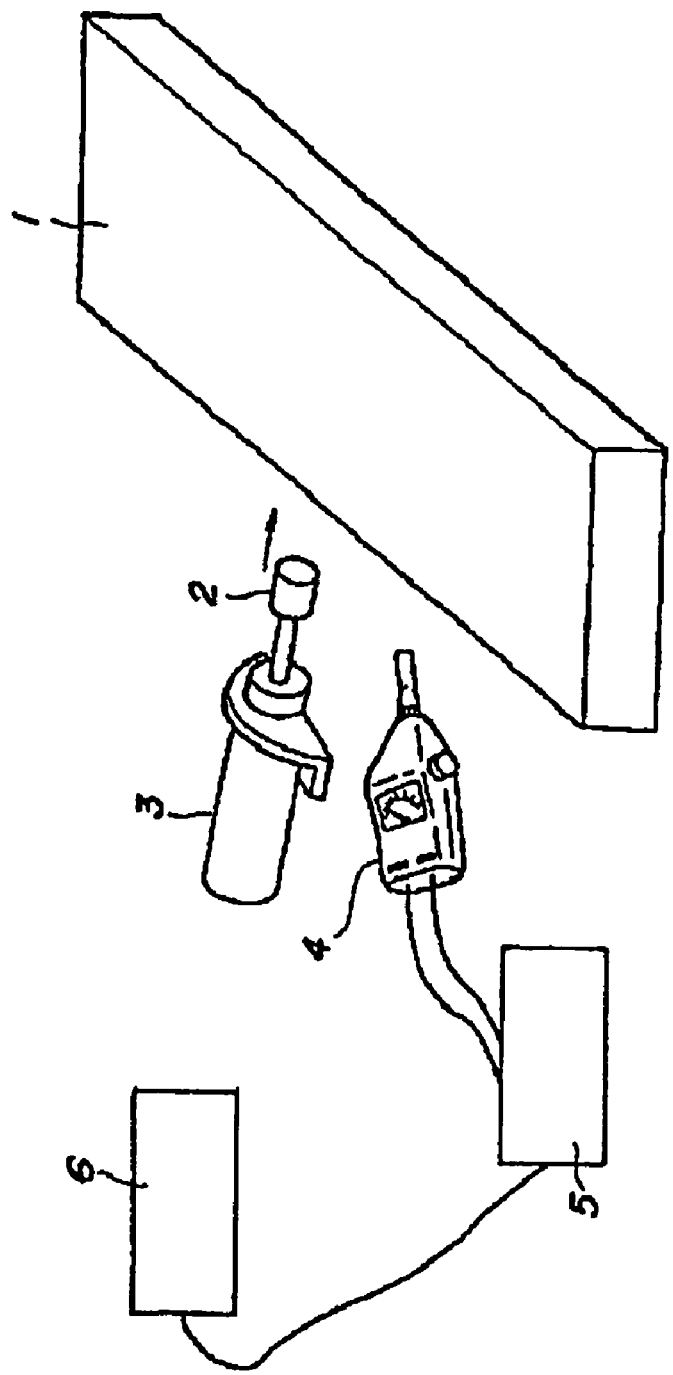
FIG. 17 is a view illustrating one example of the schematic construction of a conventional structure diagnosis apparatus.

Hereinafter, reference will be made to a structure diagnosis apparatus according to a fifth embodiment of the present invention while referring to FIG. 16. FIG. 16 illustrates another example of a display device, with the remaining construction of this fifth embodiment being similar to that of the aforementioned first embodiment.

As shown in FIG. 16, a display device 13A of this fifth embodiment is provided with a plurality of comparators $52_1$–$52_3$ arranged in parallel with each other, so that setting reference voltages for the respective comparators to different values enables the number of lit LEDs $53_1$–$53_3$ to be varied according to the amplitude of an input waveform so as to facilitate a staged or step by step display. In case of FIG. 16, the output of the amplifier 51 is dividedly supplied to respective input terminals $52_1$-1–$52_3$-1 of the comparators $52_1$–$52_3$, so that when an input voltage Vin at each input terminal exceeds the corresponding one of the reference voltages $V_1$–$V_3$ at the reference input terminals, the corresponding one of the LEDs $53_1$–$53_3$ is lit according to the above-mentioned logic. That is, by properly adjusting the reference voltages $V_1$–$V_3$, the number of lit LEDs $53_1$–$53_3$ can be varied according to the amplitude of the input waveform.

For instance, when the input voltage Vin is $V_3$<Vin<$V_2$, only the LED $53_3$ is lit; when $V_2$<Vin<$V_1$, the LEDs $53_3$ and $53_2$ are lit; and when $V_1$< Vin, all the LEDs $53_1$–$53_3$ are lit. Accordingly, the amplitude of the input waveform can be discriminated depending on the number of lit LEDs 53, whereby it becomes possible to detect the presence or absence of internal abnormalities.

INDUSTRIAL APPLICABILITY

The present invention can be utilized to objectively evaluate the internal condition (internal defects) of a structure such as a concrete structure or the like irrespective of surrounding noise or the shape of a hammer, by placing a vibration sensor in direct contact with a measuring surface so as to directly convert a vibration generated on the measuring surface into a corresponding voltage without the intervention of a medium such as air thereby to quantify the vibration generated on the measuring surface concerned.

What is claimed is:

1. A structure inspection apparatus comprising:
    a vibration unit for generating an elastic wave in a measuring object of a concrete structure;
    a vibration detector adapted to be placed in contact with a surface of said measuring object for detecting a component in a predetermined frequency range of an elastic vibration generated on the surface of said measuring object by said vibration unit, said vibration detector comprising a detection circuit that detects a maximum amplitude of an output signal of the vibration detector; and
    a display device for displaying the maximum amplitude of the output signal of said vibration detector.

2. The structure inspection apparatus as set forth in claim 1, wherein said vibration detector comprises:
    a weight;
    a spring having one end thereof connected with a contactor which is adapted to be in contact with said measuring object, and the other end thereof connected with said weight; and a vibration sensor connected with said weight for converting a vibration of said weight into a corresponding electric signal;

wherein a resonance frequency determined by a mass of said weight and a spring constant of said spring is set to be within said predetermined frequency range, so that a component in said predetermined frequency range of an elastic vibration generated on the surface of said measuring object is detected by said vibration sensor.

3. The structure inspection apparatus as set forth in claim 1, wherein said vibration detector comprises:

a spring connected with a contactor which is adapted to be in contact with said measuring object, said spring being made of a metallic material of which permeability is varied according to a bending distortion thereof;

a coil arranged around said spring which acts as a core member; and a weight connected with said spring;

wherein a bending distortion produced in said spring by an elastic vibration generated on the surface of said measuring object is detected by said coil.

4. The structure inspection apparatus as set forth in claim 1, wherein said vibration unit comprises:

a striking section for vibrating said measuring object thereby to generate an elastic wave;

a coil fixed to said striking section;

a diode connected with said coil for permitting a current to flow through said coil only in one direction; and a magnet fixedly arranged near said coil in the surroundings of said striking section for generating a magnetic field in a direction in which said coil vibrates;

wherein damping is caused only in one direction of the vibration of said striking section by means of an electromagnetic interaction between said magnet and said coil.

5. The structure inspection apparatus as set forth in claim 1, wherein said vibration unit comprises:

a striking section for generating an elastic wave on said measuring surface;

a chamber in which said striking section is accommodated; and a striking section operating mechanism for injecting a pressure medium into said chamber thereby to project said striking section outward from said chamber;

wherein said striking section operating mechanism generates an elastic wave on said measuring surface by applying thereto a fixed vibration force by means of said striking section.

6. The structure diagnosis apparatus as set forth in claim 5, wherein said striking section operating mechanism comprises: an injector for injecting a pressure medium into said chamber; and a pressure medium feeding mechanism for supplying a pressure medium to said chamber when a distance between said chamber and said measuring surface becomes a predetermined value.

7. The structure diagnosis apparatus as set forth in claim 6, wherein said pressure medium feeding mechanism comprises:

a gas cylinder for reserving said pressure medium;

a pressure regulator for regulating the pressure of said pressure medium in said gas cylinder;

a supply switch for supplying said pressure medium in said gas cylinder to said injector through said pressure regulator; and a trigger mechanism for triggering said supply switch when the distance between said chamber and said measuring surface becomes a predetermined value.

8. The structure diagnosis apparatus as set forth in claim 6, wherein said pressure medium feeding mechanism comprises:

a compressor connected with said injector for supplying said pressure medium thereto;

a supply switch for supplying said pressure medium in said compressor to said injector; and a trigger mechanism for triggering said supply switch when the distance between said chamber and said measuring surface becomes a predetermined value.

9. The structure diagnosis apparatus as set forth in claim 8, wherein said pressure medium feeding mechanism further comprises a spring having one end thereof connected with a housing of said vibration unit and the other end thereof connected with said trigger mechanism for urging said trigger mechanism in a direction away from said supply switch.

10. The structure diagnosis apparatus as set forth in claim 7, wherein said pressure medium feeding mechanism further comprises a spring having one end thereof connected with a housing of said vibration unit and the other end thereof connected with said trigger mechanism for urging said trigger mechanism in a direction away from said supply switch.

11. The structure diagnosis apparatus as set forth in claim 1, wherein said display device comprises:

an amplifier having an input terminal connected with said vibration detector and an output terminal;

a plurality of comparators each having a first input terminal connected with the output terminal of said amplifier, a second input terminal to which a reference voltage is imposed and an output terminal, said comparators being arranged in parallel with one another and each generating an output from its output terminal when an input voltage at its first input terminal exceeds the reference voltage at its second input terminal; and a plurality of display members connected with the output terminals of said comparators, respectively;

wherein the reference voltages imposed on the output terminals of said comparators, respectively, are set to different values.

12. The structure diagnosis apparatus as set forth in claim 1, wherein said predetermined frequency range of said elastic vibration is several kHz or less.

13. A structure diagnosis method for detecting an internal defect in a concrete structure, said method comprising:

a first step of generating an elastic wave on a measuring surface of a measuring object by applying a fixed force thereto;

a second step of converting a vibration generated on said measuring surface in said first step into a corresponding electric signal thereby to calculate a maximum amplitude of a component in a predetermined frequency range of said electric signal; and a third step of comparing the maximum value of said electric signal with a preset threshold thereby to detect the existence or absence of an internal defect in said structure.

14. The structure diagnosis method as set forth in claim 13, wherein said predetermined frequency range of said electric signal is several kHz or less.

* * * * *